US005948443A

United States Patent [19]
Riley et al.

[11] Patent Number: 5,948,443
[45] Date of Patent: Sep. 7, 1999

[54] ACETYLSALICYLIC ACID AND MICRONUTRIENT SUPPLEMENTATION FOR NUTRITIONAL LOSSES AND CORONARY HEART DISEASE

[75] Inventors: Patricia A. Riley; George Christakis, both of Sunrise, Fla.

[73] Assignee: Medical Doctor's Research Institute, Inc., Sunrise, Fla.

[21] Appl. No.: 08/804,494

[22] Filed: Feb. 21, 1997

Related U.S. Application Data
[60] Provisional application No. 60/012,158, Feb. 23, 1996.

[51] Int. Cl.$^6$ .......................... A61K 33/32; A61K 31/62
[52] U.S. Cl. ...................... 424/643; 424/195.1; 424/638; 424/648; 424/655; 424/656; 424/687; 424/692; 514/52; 514/161; 514/162; 514/163; 514/164; 514/165; 514/167; 514/168; 514/249; 514/251; 514/276; 514/345; 514/356; 514/387; 514/440; 514/456; 514/458; 514/474; 514/494; 514/499; 514/500; 514/502; 514/505; 514/556; 514/557; 514/561; 514/563; 514/578; 514/678; 514/725; 514/729; 514/762; 514/904; 514/905
[58] Field of Search ...................................... 514/165, 904, 514/905, 52, 161, 162, 163, 164, 167, 168, 249, 251, 276, 345, 356, 387, 440, 456, 458, 474, 494, 499, 500, 502, 505; 424/643, 195.1, 638, 648, 655, 656, 687, 692

[56] References Cited

U.S. PATENT DOCUMENTS

| | | |
|---|---|---|
| 4,158,705 | 6/1979 | Malley . |
| 4,826,679 | 5/1989 | Roy . |
| 4,976,960 | 12/1990 | Grossman et al. . |
| 5,118,505 | 6/1992 | Koltringer . |
| 5,256,538 | 10/1993 | Aiken et al. . |
| 5,356,636 | 10/1994 | Schneider et al. . |
| 5,514,382 | 5/1996 | Sultenfuss . |
| 5,571,441 | 11/1996 | Andon et al. . |
| 5,626,849 | 5/1997 | Hastings et al. . |
| 5,648,377 | 7/1997 | Bombardelli et al. . |
| 5,654,011 | 8/1997 | Jackson et al. . |

OTHER PUBLICATIONS

U.S. Department of Health and Human Services, Healthy People 2,000: National Health Promotion and Disease Prevention Objectives, Dept. of Human Services, Conference Edition, Sep. 1990—Part I; Part II: Introduction, Ch. 2 Nutrition, Ch. 5 Heart Disease and Stroke.
Jialal, A. et al., J. Nutr. 126: 1053S–1057S, 1996.
Maggi, E., M.D., et al., Coronary Artery Disease 4(12): 1119–1122, 1993.
Hirose, N. et al., Keio J Med 45 (2): 90–94, 1996.
Levy, Y. et al., Isr J Med Sci 32: 473–478, 1996.
Preobrazhensky, S. et al., Analytical Biochemistry 227(1): 225–234, 1995.
Mackness, M. et al., Biochem J.: 294: 829–834, 1993 (Printed in Great Britain).
Porkkala–Sarataho, E., et al., Atherosclerosis 124(1): 83–94, 1996.
Jialal, I., M.D. et al., Circulation 88: 2780–2786, 1993.
Frei, B., Critical Reviews in Food Science and Nutrition 35(1&2) 83–98, 1995.
Halliwell, B., Am J Clin Nutr; 61 (3) 670S–7S, 1995.
Helzlsouer, K. et al., Cancer Research, 54 (7 Suppl): 2044S–2051S, 1994.
Stahelin, H.B. Supportive Care in Cancer 1(6): 295–7, 1993.
Bartosiewicz, G. et al, Therapia Hungarica 41(2):67–71, 1993 (English Abstract Only).
Hallfrisch, J. et al., Am J Clin Nutr 60(2): 176–82, 1994.
Statistical Bulletin of Metropolitan Ins. Co., 73(3): 2–9, Jul.–Sep. 1992.
Schroll, M., Danish Med Bull 39(3): 258–61, 1992.
Sohal, R. et al., Mechanisms Of Aging and Development 53(3): 217–227, 1990.
Nutritional Checklist, Nutrition Screening Initiative, Washington, D.C., 20037, pp. 1–3, 1994.
Fairbanks, V., in Modern Nutrition in Health and Disease, 8th Edition, vol. I, Ch. 9, 1994.
Reynolds, J., et al Calc. Tiss. Res. 12, 295–301, 1973.
Chandra, R., M.D., JAMA 1984; 252:1443–46.
King, J. et al., in Mod Nutr in Health and Disease, 8th Edition, vol. I, Ch. 10, 1994.
Meydani, S., Nutrition Reviews, 51(4): 106–115, 1993.
Chandra, R., Lancet 340: 1124–27, 1992.
Meydani, S. et al., Am J Clin Nutr; 53(5): 1275–80, 1991.

(List continued on next page.)

*Primary Examiner*—Minna Moezie
*Attorney, Agent, or Firm*—Holland & Knight LLP

[57] ABSTRACT

The present invention pertains generally to the field of Public Health, including the prevention and treatment of coronary heart disease which is currently the first cause of death in the American population. More specifically, the present invention concerns a total modular system of multivitamin and mineral supplementation composed of 7 distinct modules for improving public health by insuring adequate intake of micronutrients needed for disease prevention and protection against nutritional losses and deficiencies due to, for example, lifestyle factors and common inadequate dietary patterns. A module, as used herein throughout, is defined as a separate and distinct combination of vitamin-mineral and other health promoting compounds which are directed to specific target populations. The formulations of the present invention which, when combined in one capsule or tablet or as separate modules, exert a joint and enhancing effect on the major pathogenetic factors involved in the atherosclerotic process. Moreover, certain modular formulations of the present invention incorporate both antioxidants and acetylsalicylic acid (aspirin) as a single preventive modality. Such a combination of antioxidants and aspirin is believed to act to prevent oxidation of low density lipoproteins within coronary arterial walls and to cause platelet deagluttination thereby inhibiting thrombus formation. The benefit of preventing these two major processes is believed to reduce the risk of coronary heart disease.

1 Claim, No Drawings

OTHER PUBLICATIONS

Malkowska–Zwierz, W. et al., Archivum Immunologiae et Therapiae Experimentalis 39(1–2): 109–15, 1991 (English Abstract Only).

Meydani, S., Am J Clin Nutr 53(4): 984, 1991.

Dhur, A. et al., Comp. Biochem. Physiol, 96C(2): 271–280, 1990.

Blomhoff, H. et al., The Journal of Biological Chemistry, 267(33):23988–23992, 1992.

Garbe, A. et al., J. Exp Med., 176(7): 109–117, 1992.

Buck, J. et al., J. Exp. Med. 171: 1613–1624, 1990.

Prabhala, R. et al., Cancer 67(6):1556–1560, 1991.

Porsova–Dutoit, I. et al., Endocrine Regulations, 27: 75–82, 1993.

Kreutz, M. et al., Blood, 76(12): 2457–2461, 1990.

Jacob, R. et al., Am J Clin Nutr, 54(6): 1302S–9S, 1991.

Kramer, T. et al., Am J Clin Nutr, 58(4): 566–70, 1993.

Trujillo. E., Journal of Vascular Nursing, 11(1): 12–18, 1993.

Goode, H. et al., BMJ 305: 925–7, 1992.

Maderazo, E. et al., The Journal of Trauma, 31(8): 1142–50, 1991.

Brolin, R. et al., International Journal of Obesity, 15(10), 661–667, 1991.

Ngyen, T. et al., J Burn Care Rehabil; 14(6): 602–9, 1993.

National Institutes of Health, 5(3): 421–132, 1984.

NIH, NIH Consenssus Statement, 12(4): 1–31, 1994.

Offenbacher et al., Diabetes, 29: 919–925, 1980.

Steering Committee of the Physicians Health Study Research Group, The New England Journal of Medicine, 321(3): 129–135, 1989.

Kendrick, Z.V. et al., in Exercise, Nutrition, and Energy Metabolism, Chapter 14, 1988.

Violi, F. et al., Atherosclerosis, 82: 247–252, 1990.

Hockertz, S. et al., Arzneim–Forsch. 42: 1062–8, 1992.

Zhen, G. et al., Acta Pharmacologica Sinica, 14(3): 263–265, 1993 (English Abstract Only).

McAlindon, M. et al., Gut 38(4): 518–24, 1996.

Hennekens, C., Am Heart J 128: 1333–6, 1994.

Vasconcellos C. et al., Blood 82(12): 3648–3657, 1993.

Lee S. et al., Vet Human Toxicol 37(3): 224–5, 1995.

Lotzerich, H. et al., Anticancer Research 13(1), 87–92, 1993.

Brouard, C. et al., Ann Nutr Metab 37(3): 146–159, 1993.

Claria, J. et al., Proc. Natl. Acad. Sci. USA, 92(21): 9475–9479, 1995.

Ames, B. et al., Pro. Natl. Acad. Sci. USA, 90: 7915–7922, 1993.

Manson, J. et al., Ann Epidemiol, 5: 261–269, 1995.

Christakis, G., in Nutrient Additions to Food, Chapter 18, 1990.

Steiner M. et al., Biosis Abstract 96: 65876, Doc. #98638011, 1995.

Schatzkin, A. et al., Biosis Abstract 95: 456683, Doc. #98470983, 1995.

Biosis abstract 96: 65876, Document No. 98638011, (1995) Steiner, M. et al.

Biosis abstract 95: 456683, Document No. 98470983, (1995) Schatzkin, A. et al.

ACETYLSALICYLIC ACID AND MICRONUTRIENT SUPPLEMENTATION FOR NUTRITIONAL LOSSES AND CORONARY HEART DISEASE

CROSS REFERENCE TO A RELATED APPLICATION

This application for U.S. patent is a U.S.C., Title 35, §111(a) application which is based on a co-pending U.S.C., Title 35, §111(b) U.S. provisional application, Ser. No. 60/012,158. Therefore, pursuant to 37 CFR §1.78(c), reference is made to and priority is claimed from U.S. provisional application, Ser. No. 60/012,158, which was filed on Feb. 23, 1996, which is pending and which is entitled "Methods & Micronutrient Compositions for use as Nutritional Supplements."

FIELD OF THE INVENTION

The present invention concerns a total modular system of multivitamin and mineral supplementation composed of 7 distinct modules for improving public health by insuring adequate intake of micronutrients needed for disease prevention and protection against nutritional losses and deficiencies due to, for example, lifestyle factors and common inadequate dietary patterns. A module, as used herein throughout, is a separate and distinct combination of vitamin-mineral and other health promoting compounds which are directed to specific target populations.

BACKGROUND

Micronutrients are elements or compounds which are present in foods in small or trace amounts and includes vitamins, minerals or other elements; and compounds found in foods for which a Recommended Dietary Allowance (RDA) has not yet been determined (pantothenic acid, biotin, choline, etc.). The macronutrients consist of carbohydrates, fats and proteins which supply nutrients and calories. Some elements such as calcium, sodium, potassium, chloride and phosphorus are elements consumed in relatively large amounts, while many such as iron, iodine, and zinc are consumed in small amounts (milligrams). Vitamins such as vitamin B12, and folic acid and the minerals copper, selenium and chromium are consumed in very small, or trace amounts (micrograms). Inasmuch as the human body, does not synthesize many "essential compounds", these specific vitamins and minerals can be obtained from only two sources: foods and supplements. The primary source of all nutrients is food. Over the past four decades, ample evidence documents that major portions of various subgroups of Americans stratified by age, gender, socioeconomic status and other variables, cannot meet the "Recommended Dietary Allowances" of the foods containing these essential compounds and elements. Thus vitamin and mineral supplementation has become a recognized method of meeting accepted medical and public health nutrition standards. The enrichment of bread with iron and B vitamins in 1940 is considered a major factor in assuring favorable nutritional status for the general population of that time, and has been retained as a major advance for public health. In 1993, the Interagency Board of Nutrition Monitoring and Related Research reported that women did not meet the RDA's of 6 out of 15 micronutrients: B6, E, calcium, iron, magnesium and zinc. Men also failed to met the RDA's for 4 of 15 micronutrients: B6, E, magnesium and zinc. Their findings reveal significant prevalence and incidence of various population subgroups deficient in specific vitamins and minerals. The importance of these findings relate to the prevention of micronutrient deficiency diseases such as scurvy (vitamin C deficiency), pellagra (niacin deficiency), beri-beri (vitamin B1 deficiency), iron deficiency anemia and other vitamin and mineral deficiency states. The effect of marginal deficiency states is only now being considered as a cause of suboptimal health status. Moreover, research conducted and published in the past three decades indicates that antioxidant micronutrients are involved in preventing molecular biological processes affecting health and disease at the subcellular and submolecular level. It is current thought that free-radical effects on cells and tissues can be modified by antioxidant micronutrients reducing cellular damage. Specific micronutrients maintain immune system integrity, moderate the aging process, and play a role in the prevention of atherogenesis and cancer.

Furthermore, substantial segments of the population do not manifest desirable eating patterns, that is, an adequate intake in both the quantity and variety of food to fulfill the Recommended Dietary Allowances, as indicated by recent government survey. Only 22% of the subjects of a National Cancer Institute Study, consumed the recommended number of dietary servings of fruits and vegetables.

Lifestyle factors such as smoking, levels of physical activity, exposure to toxic environmental compounds, dieting, use of certain medications such as oral contraceptives, and the avoidance of certain foods (for example, due to lactose intolerance which occurs in over 25% of the population), can also contribute to low or deficient intakes of nutrients.

It has been further documented that the American public is unaware of the importance of public health nutrition recommendations. Only 8% of adults eat the recommended number of daily servings of fruits and vegetables. Micronutrient deficient states may be recognized by physicians, nutritionists and dietitians who are trained in clinical nutrition. However, the physical findings of a nutritional deficiency can be subtle, and physicians may not be trained in detecting them. The use of laboratory methods to assess nutritional status, which includes blood and tissue levels of vitamins and their effects (A, C, E, D, etc.) on various enzyme systems (B1, B2, B6), is often considered the most reliable method of assessing nutritional status, though these special testing procedures are expensive and do not exist in standard medical offices or in many hospital clinical laboratories. Thus the invention of an easily accessible formulation which supplies nutrients that help prevent the most commonly seen deficiencies would benefit the public.

In the last decade it has also been determined that "marginal" vitamin and mineral deficiency states occur, in which the blood or tissue levels are in the "low" range, without the presence of physical signs of deficiency, but which may induce symptoms of fatigue, lassitude, and a general sense of ill health. It is thus clear that nutrition science has progressed in defining its role in health, and that the role micronutrients play in health and in disease prevention is indeed substantial and gratifying.

However, because of the special training required for qualified and certified nutrition assessments, the expenses involved, and the time required to conduct the necessary history taking, physical examination and appropriate laboratory testing, it is apparent that consumers are forced into making their own nutrient supplement choices. Currently there are a plethora of over-the-counter vitamin and mineral supplements which fail to completely consider the extensive nutrition science literature. These are based on a "shot-gun" approach of supplying 100% of the Recommended Dietary Allowances for some of the micronutrients for which an (RDA) exists, fail to consider the consumer's dietary contribution of vitamins and minerals, and often provide unproven ingredients, inadequate dosages of important nutrients, and megadoses without a scientific rationale.

The multi-vitamin formulations available heretofore are designed without consideration for micronutrient interactions. Examples of the significance of these reactions is the required presence of optimal vitamin C for the absorption of iron, the presence of Vitamin D for the absorption of calcium, and the mutually protective effects of vitamin A and E. Another problem is that many of the multi-vitamin formulations today do not take into account the different dietary allowances and needs for men and women. In addition, most multi-vitamin formulations currently available require once-daily dosing which do not take into consideration loss of water soluble nutrients which are not well stored by the body and are utilized in energy-yielding reactions during the day. Moreover, many multi-vitamin formulations on the market are haphazardly self-designed to supply megadoses of potentially toxic amounts of nutrients, such as vitamin A, vitamin D, vitamin B6, iron, zinc and copper. Other commercially available vitamin formulations contain unnecessary and potentially allergic compounds, such as dyes, fillers and sugars like lactose.

Public health nutrition can be considered a "two-edged sword." One edge represents nutritional deficiencies such as protein-energy, malnutrition, the hypovitaminoses, nutritional anemias, osteoporosis, iodine deficiency and other specific deficiencies. The other "edge" are the nutritional excesses and determinants of major diseases. These excesses include calories, saturated fats, total fat, dietary cholesterol, sodium, and alcohol, as well as insufficient dietary fiber, potassium, iron and antioxidant micronutrients (Vitamins A, C, E, selenium, zinc, carotenoids etc.).

Many Americans get less than 70% of the recommended daily allowances for many nutrients. The public health importance of older populations is emphasized by a World Health Organization report indicating that by the year 2000 those over 60 will reach 17% of the total population.

Moreover, the work of experimental and clinical pathologists have identified the histological and subcellular changes which take place to induce atherosclerosis in experimental animals and man. The emerging concept is that oxidized low density lipoprotein (LDL) is the key initiating agent in atherogenesis, since contrary to normal LDL, oxidized LDL is rapidly attacked by scavenging receptor macrophages which, in turn, incite the production of lipidladen foam cells. These cells comprise the "fatty streak," which is the first macro tissue change in arterial endothelium and intima. The effect of the oxidized LDL is cytotix to endothelial cells. It causes increased cell membrane permeability, which allows more oxidized LDL to enter the cells, increases the permeability of endothelial cells which thus makes them pervious to nicotine, and norepinephrine release due to psychological stress, and other noxious compounds which increase the risk of coronary heart disease. These findings assumed new significance when it was discovered that the oxidation of LDL could be prevented significantly by micronutrient antioxidants such as beta carotene and vitamin E.

The original concept that nutrients could effect biological and physiological systems began with the study of the aging process. Intracellular oxidative reactions in brain cells were found to play a major role in the aging process. Animal and human studies gave further impetus to these findings when it was shown that specific micronutrients, notably vitamin E, substantially blocked the induction of free radicals. Later, it was documented that lipid peroxidation formed free radicals with release of free-spinning electrons which injured delicate subcellular organelle structures such as mitochodrial membrances. This, in turn, caused release of enzymes and other toxic compounds into the cytisol which induces further injury. As related to atherogenesis, both oxidized LDL and peroxidation of fatty acids are now considered to induce macrophage and other cells to transform into foam cells which comprise the fatty streak, the earliest histologically detectable origins of coronary atherosclerosis, as cited above.

The atheroscelrotic plaque forms when there is proliferation of foam cells, invasion of the histological environment with calcium, and distortion of the normal cellular architecture of the coronary artery. Moreover, the normal endothelial cell is also injured in this process, and the once smooth internal surface of the artery now becomes roughened. It is upon this surface that platelets can become adherent, and aggregate to initiate the formation of a thrombus. When the plaque is hardened, an edge of it may break away from the endothelium to which it adheres. This makes it open to the shearing effect of blood, to which more platelet aggregation can cause the clot to enlarge and thus further restrict the arterial flow; or in some instances the shearing effect of blood can "dissect out" the plaque and convert it to an embolus blocking the artery. Both events can result in myocardial infarction.

Consequently, there still exists a need for a nutritional system which supplies the right amount of the right micronutrients at the right time to help prevent the problems commonly seen with vitamin supplementation available today and to assure adequate intake of micronutrients needed for disease prevention and protection against nutritional losses and deficiencies due to, for example, lifestyle factors and common inadequate dietary patterns.

SUMMARY OF THE INVENTION

In brief, the present invention alleviates and overcomes certain of the above-mentioned drawbacks and shortcomings through the discovery of a novel modular system of multi-vitamin and mineral supplementation composed of 7 distinct modules. Generally speaking, a module, as used herein throughout, is defined as a separate and distinct combination of vitamin-mineral and other health promoting compounds which are directed to specific target populations.

More specifically, Module 1, the basic formula, is directed to the general public and consists of vitamins and minerals essential for the prevention of vitamin and mineral deficiency diseases and for the promotion of general good health. It is gender-specific, with certain amounts given to fulfill the defined nutrient requirements of men and women, and with an AM and PM modality.

Module 2 is a Stress formula directed towards supplying the needs of persons during periods of physical and emotional stress, and for support of the immune system during and recovering from illness.

Module 3 is committed to implementing the public health goals and priorities, including national health promotion and disease prevention objectives as cited in Healthy People 2000 published by the U.S. Department of Health and Human Services. Healthy People 2,000: National Health Promotion and Disease prevention Objectives. Dept. of Human Services, Conference Edition, September 1990. It is the basis for this invention's fulfilling the dire need for preventive medicine, by assisting in the reduction of risk factors of chronic disease such as coronary heart disease and cancer. It contains not only the basic daily nutrient needs, but specific doses of vitamin, minerals and other compounds, such as antioxidants and folic acid, which have been found to reduce some of the nutritional determinants of these diseases.

Module 4 contains aspirin or the like at four varying dosages, and is directed primarily for persons known to be at risk of coronary heart disease or other diseases which may be favorably modified by aspirin, and which provides specially formulated dosages to reduce the risk of heart attack.

Module 5 is essentially Module 1 combined with about 20 mg of aspirin within the AM tablet.

Module 6 is also essentially Module 1, but combined with about 81 mg of aspirin with the AM tablet.

Module 7 which is the same as the low dose formulation in Module 3, but combined with about 81 mg of aspirin.

The novel formulations presented in accordance with the present invention provide the right amount of the right micronutrients at the right time to avoid and overcome the problems commonly seen with vitamin supplementation today. Also in accordance with the present invention, there is a separate formula for men and women to address their different needs. Still further, the evening formulas of the instant invention are designed to allow for the absorption and storage of fat soluble nutrients, as the evening meal is usually higher in fat content.

Thus the primary and secondary prevention and treatment of coronary disease must rely simultaneously on two points of therapeutic attack: the provision of antioxidants to prevent free radical formation by the immediate and sustained availability of nutrient antioxidants, and the antiplatelet aggregating capacity of acetylsalicylic acid (aspirin). Thus, the combined use of both antioxidants and aspirin is utilized by the formulations of the present invention as the two "edges" of a double-edged sword of prevention.

Also in accordance with the present invention, a method is herein provided for the prevention and treatment of atherosclerosis-induced coronary heart disease. This method embodies the combination of nutrient antioxidants and aspirin as the present invention, which meets criteria required to successfully intervene in the atherosclerotic process. Oxidized low density lipoprotein (LDL) macrophage scavenger infiltration into damaged epithelial sites promotes the attraction of monocyte-macrophages, T-lymphocytes, formation of foam cells, myointimal cells, fibroblasts and smooth arterial muscle cells which proliferate in the arterial intima. Injured epithelial cells invoke platelet thrombi formation which also participate in the atherosclerotic process. Jialal, I. et al. (1996) J. Nutr. 126: 1053S–7S. The relevance of oxidized LDL to atherosclerosis was further enhanced when it was shown in humans that specific autoantibodies to oxidized LDL were discovered in the plasma of persons with coronary atherosclerosis, and the levels were related to the degree of the progression of their atherosclerosis. Maggi, E., et al. (1993) Cor. Art. Dis. 4(12): 1119–1122.

However, antioxidiants are believed to prevent macrophage scavenger receptors from entering potential atherosclerotic sites on the inner surfaces of arteries. Hirose, N., et al. (1996) Keio J. Med. 45(2): 90–94. The nutrient antioxidant beta-carotene decreases human macrophage LDL oxidation by 40%. This action helps prevent the atherosclerotic lesion by blocking cholesterol ester accumulation and foam cell formation, thus deterring the formation of the atherosclerotic plaque. Levy, Y. et al. (1996) Isr. J. Med. Sci. 32(6): 473–478. Furthermore, oxidized LDL is believed to be linked with apoprotein B, for which there is substantial clinical and epidemiological data as a recognized risk factor for coronary heart disease. Apoprotein B is believed to be inhibited in the presence of various antioxidants. Preobrazhensky, S., et al (1995) Anal. Biochem. 227(1): 225–34. Antioxidant supplementation also appears to inhibit LDL oxidation in humans by significantly reducing diene formation. Mackness, M. I., et al. (1993) Biochem. J. 294 (Part 3): 829–834. Dietary vitamin E levels in the serum were studied in relation to in vitro oxidation of LDL and VLDL, and were found to confer significant protection against the oxidation of these atherogenic lipoproteins. Porkkala-Sarataho, E., et al. (1996) Atherosclerosis 124(1) :83–94. High dose alpha-tocopherol is also believed to be effective in inhibiting LDL oxidation, as compared to other antioxidants. Jialal, I., et al. (1993) Cirulation 88(6) :2780–2786. The pathogenetic role of LDL, and the ability of antioxidants to have favorable effects in deterring or reducing coronary atherosclerosis has been also recently summarized. Frei, B. (1995) Crit. Rev. in Food Sci. & Nut 35(1–2): 83–98; Halliwell, B. (1995) Am. J. Clin. Nutr. 61(3 Suppl): 670S–677.

Also in accordance with the present invention, it has been discovered that "low dose" aspirin therapy on a daily basis unexpectedly and suprisingly achieves platelet deagglutination thereby inhibiting thrombus formation without causing severe prolongation in blood clot times. In other words, it is now possible to achieve the benefits of aspirin therapy, i.e., reducing atherosclerotic plaque formation and the risk of coronary heart disease, at low daily dosages not known or utilized without the negative side effects, i.e., ulceration and prolonged bleeding times, commonly associated with higher dose daily aspirin therapy. By "low dose," it is meant herein that aspirin is consumed at a daily dosage of less than about 30 mg and more preferably at a daily dosage of about 20 mg. or less.

It should also be understood that Modules 1–3 of the present invention may be administered together or independent of one another, or in any suitable combination such as Modules 1 and 2 may be taken together, or Modules 1 and 3 may be taken together, or Modules 2 and 3 may be taken together. It should also be understood that Modules 1, 2 or 3 may be taken alone without the other Modules. It is believed, however, that the benefits of Modules 2 and 3 are maximized when Module 2 is taken concomitantly with Module 1 and when Module 3 is taken concomitantly with Modules 1 and 2. While Modules 2 and/or 3 may be taken at times different from Module 1 and one another, it is believed that maximum benefits are achieved when Modules 2 and/or 3 are taken with the AM or PM dosages of Module 1.

As to Modules 4–7, it is likewise believed that the benefits of such therapy are maximized when Modules 4, 5, 6 and/or 7 are taken in conjunction with Modules 1, 2 and/or 3. Moreover, the present invention contemplates Modules 1–3 actually containing in their formulations aspirin such as set forth in Modules 5–7, see Tables II and III, or Modules 1–3 being taken in conjunction with separate aspirin dosage forms.

Thus, the novel nutritional modular systems of the present invention are therefore helpful toward improving the general public health by contributing to the reduction of nutritionally determined risk factors for chronic disease, thereby helping to prevent illness, disability and death due to diseases such as Syndrome-X and diabetes. Moreover, since coronary heart disease and cancer are the major causes of death, the nutritional determinants of these diseases and the ability to maintain immune competence through the use of the novel multi-vitamin, mineral, and antioxidant formulas of the present invention can play a major role in contributing to public health. The formulas of the instant invention can also help fulfill the RDA's in persons who are not meeting them by dietary means. Still further, the present invention utilizes the protective effects of antioxidant micronutrients to help prevent diseases responding to these compounds and prevents nutritional deficiencies which otherwise could result in immune system impairment, greater risks of infections and other illnesses which may decrease health and longevity.

It should now be readily apparent to those versed in this art that the present invention provides a unique system for improving public health by insuring adequate intake of nutrients needed for disease prevention, which will advantageously contribute to a decrease in cost of medical care, especially for the elderly. In addition, through the reduction of the risk of many diseases, the present invention will contribute to an increase in healthy and active life spans.

DETAILED DESCRIPTION OF THE INVENTION

By way of illustrating and providing a more complete appreciation of the present invention and many of the attendant advantages thereof, the following detailed description and examples are given concerning the novel modular systems of multivitamin and mineral supplementation of the present invention.

As indicated above, the present invention concerns a total modular system of multivitamin and mineral supplementation composed of 7 distinct modules for insuring adequate intake of micronutrients needed for disease prevention and protection against losses and deficiencies due to, for example, lifestyle factors and common inadequate dietary patterns.

Module 1 of the present invention has the capability of providing an antioxidant vitamin-mineral formula with an AM and PM dosage, which allows enhanced and sustained absorption and utilization of micronutrients which are essential for (i) normal metabolic functioning as cofactors in many pathways of carbohydrate, fat and protein metabolism, (ii) the prevention of vitamin and mineral deficiency diseases which thus allows optimal daily nutritional, physiologic and metabolic functions which promoting wellness and avoid deficiency symptoms, such as fatigue and general malaise, (iii) the synthesis of compounds, such as neurotransmitters, and other physiological compounds for the metabolic reactions required to maintain health, (iv) decreasing the negative effects of free radical reactions which play a pathogenic role in diseases of major public health importance, such as coronary heart disease and cancer, thus contributing to an increased active life span, (v) decreasing homocysteine levels which may reduce the risk of coronary heart disease, (vi) decreasing the risk of diseases linked to suboptimal intakes of carotenoids by the presence of beta-carotene and alpha-carotene for their role in immune function, lutein to decrease the risk of macular degeneration, and lycopene to decrease the risk of prostate, breast and other cancers, and skin damage secondary to ultraviolet exposure, (vii) maintaining antioxidant/vitamin/mineral tissue levels throughout the day and night, (viii) health maintenance in men and women with formulation modifications to optimize benefits for each gender, and (ix) the optimization of wellness for individuals with varying lifestyle factors and states of health, with inclusion of: (a) an add-on stress Module 2 for those under physical or mental stress who require more nutrients; (b) an add-on coronary heart disease, Module 3, which may also apply to other conditions as well where higher dosages of specific nutrients may be necessary; or (c) an add-on Aspirin, Module 4, when indicated, with varying dosages designed to enhance the health benefits of the micronutrients and the aspirin.

The AM/PM formula in Module 1 is designed for use with aspirin so that the micronutrient dosages and precise combinations in the formula function both independently and synergistically with aspirin to provide definitive health advantages.

The add-on modules of the formulation allow the Module 1 AM/PM formula, Module 2, one of the variations of Module 3, and Module 4, to be taken together as may be indicated.

Module 5, 6 or 7 may be taken with Module 2 and/or one or both of the variations of Module 3.

The Module 1 formulation, see Tables II and III, provides a nutritional supplement that contributes to increased health and active life span by insuring optimal intake of nutrients in appropriate levels and combinations to insure protection against nutritional losses and deficiencies, due to lifestyle factors and common inadequate dietary patterns while optimizing the defenses of protective nutrients and compounds which may decrease risk of chronic diseases, such as cited above.

The Module 1 formulation also considers lifestyle factors, such as smoking, elevated blood cholesterol, obesity, psychological stress, intensive exercise, intake of smoked foods containing nitrosamines and use of certain medications which increase requirements for nutrients. For example, exercise increases the need for vitamin B2 and chromium. Smoking increases the need for vitamin C. Niacin influences cholesterol metabolism. Chromium potentiates insulin function which affects blood sugar levels.

Furthermore, the Module 1 formulation considers environmental factors which contribute to the aging process including the effects of solar radiation, pollution and other toxicants. For example, vitamin C maintains healthy connective tissue, and vitamin E, and the carotenoids, especially lycopene, protect against ultraviolet radiation.

The Module 1 formulation considers dietary factors which contribute nutritional risk factors to chronic disease. For example, use of a low saturated fat, low cholesterol, high fiber, high fish intake diets are capable of decreasing serum cholesterol in free-living populations, and thus decrease coronary heart disease incidence, and increase longevity. However high fiber diets can deplete minerals such as calcium, zinc and iron which are provided in the formula. Increasing intake of dietary Vitamin E and other polyunsaturates increases the need for antioxidants, these micronutrients are provided for in the formulation.

The Module 1 formulation contains a unique combination of antioxidants and nutrients which allow specific antioxidant enzymes to be produced in the body. This protects against specific pathological processes spontaneously generated by biochemical reactions which induce intracellular lipid peroxidation and free radical formation. This contributes to disease and early mortality. For example, oxidized low density lipoproteins contribute to atherosclerotic plaque formation; and unprotected ozone-free "holes" in the atmosphere permit gamma and other radiation to induce free radical formation and their injurious effects. The Module 1 formulation provides dosages of antioxidants which protect against these free radical reactions.

The Module 1 formula further helps prevent deficiencies of essential and non-essential micronutrients that play important roles in intracellular metabolic processes and immune competency. Maximum life span depends on how well a person's total organ system can effectively maintain an immune defense system against toxic environmental compounds, infectious disease, and sustain the individual's ability to cope with genetically determined disease processes, and live a healthy lifestyle.

The Module 1 formulation also contributes to increased longevity as follows: as many people age, their nutritional status declines as their dietary intake decreases due to illnesses, poor dentition, inadequate funds, inability to shop, etc., change in a direction that contributes to micronutrient deficiencies which affect the immune system. Premature aging as well as chronic diseases may foreshorten life and can be prevented to some extent by dietary intake. Considering the immune status of elderly persons, T-lymphocytes, B-cells and IgM production are significantly decreased when compared to younger adults. Furthermore, an individual's diet may not fully provide the antioxidants that will help in the prevention of coronary heart disease, the paramount cause of premature death. By assuring adequate dietary supplementation, this Module 1 formulation of micronutrients (vitamin and minerals) which are cofactors required for the synthesis of immune compounds, and also act as antioxidants, may reverse this trend and result in an enhanced, more physiologically efficient immune system and improved total body function.

The Module 1 formulation provides nutrients which may help decrease the risk of cancer. Cancer may well gain first place in adult mortality rates in the next decade. A review of the relationship of diet to cancer, coronary heart disease and longevity, Helzlsouer, K. J, et al. Summary of the Round Table Discussion on Strategies for Cancer Prevention: Diet, Food, Additives, Supplements, and Drugs (1994) [Review]. Cancer Research, 54 (7 Suppl): 2044s–2051s, cites that diet contributed to the causes of 50% of all cancers by inducing cancer promotion. In addition, public health recommendations have been made for the public to consume a low fat diet (25% of total calories), 20–30 grams of fiber, and 5 servings of fruits and vegetables daily. Lack of host resistance increases the risk for cancer, thus acting as a promoter. Vitamins A, B6, C, and E and the minerals selenium and zinc in appropriate dosages can restore and maintain immunocompetence, and have been recommended as dietary supplements. Helzlsouer, K. J, et al. Summary of the Round Table Discussion on Strategies for Cancer Prevention: Diet, Food, Additives, Supplements, and Drugs (1994) [Review]. Cancer Research, 54 (7 Suppl): 2044s–2051s, and Stahelin, H. B., Critical Reappraisal of Vitamins and Trace Minerals in Nutritional Support of Cancer Patients. Supportive Care in Cancer, 1(6): 295–7, 1993. This Module 1 formulation provides these nutrients in a novel AM and PM dosage system along with other synergistic nutrients.

Antioxidants in the Module 1 formulation are also associated with protection against degenerative diseases which occur as aging progresses. See Bartosiewicz, G. et al, Changes in Lipid, Peroxide and Anti-oxidant Blood Levels During Piroxicam (Hotemin) Treatment. Therapia Hungarica 41(2): 67–71, 1993; and Hallfrisch, J., Muller, D. C, Singh, V. N., Amer. Jour. of Clin. Nut. 60(2), 176–82, 1994. Given the evidence linking intake of antioxidants to reduced risk of coronary heart disease, certain cancers, cataracts, and macular degeneration, many persons should be considered as candidates for antioxidant enhancement as provided by this unique formulation.

Life expectancy in the U.S. for boys in 1991 was 72 years, and for girls 78.8 years. See Statistical Bulletin of the Metropolitan Insurance Companies, 73(3): July–September, 1992. The U.S. ranks 11th in life expectancy (75.4 years) with Japan first at 78.9 years. Nutrition patterns in regions of high longevity in Russia suggest that increased carbohydrate and fiber intake, and increased "geroprotective" micronutrient intakes in addition to reduced consumption of total dietary proteins and saturated fat, may be associated with longevity in that region. See Schroll, M., Danish Medical Bulletin 39(3): 258–61, June 1992.

Animal studies have shown that the maximum life span of 6 mammalian species can be correlated with the concentration of antioxidants, and the enzymes superoxide dismutase (SOD), catalase, and glutathione peroxidase, in the liver, heart and brain. See Sohal, R. S., Sohal, B. H., Brunk, U. T., Mechanism of Aging & Development 53(3): 217–27, Apr. 30, 1990. These enzymes require the presence of certain nutrients (zinc, copper, manganese, iron and selenium) which are provided in this Module 1 formulation. Deficiencies of selenium in certain regions of China has been related to reduced life span in the 35–45 age group.

Recent nutrition surveys in Japan comparing Okinawa which has the longest lifespan among Japanese, and Akita where the lifespan is much shorter, reveal that Okinawans' intake of antioxidants vitamins A and C, as well as the nutrients B1, B2, calcium and iron were significantly higher, while their carbohydrate and salt intake was lower. The composition of the Module 1 formulation takes into account higher levels of antioxidant nutrients and other geroprotective nutrients than is found in ordinary multivitamin-vitamin preparations.

Animal and human studies postulate that life expectancy at birth may be increased by 5 or more years by a low fat, high carbohydrate eating pattern supplemented by one or more micronutrient antioxidant nutrients. Thus, the use of this unique Module 1 composition on a daily basis contributes to increased longevity by insuring adequate intake of nutrients designed to optimize their interactions to obtain, greater health benefits than those documented by each nutrient individually.

The unique and original vitamin and mineral Module 1 formulation system of the present invention is further based on criteria not previously considered such as:

1. vitamin-vitamin interactions,
2. vitamin-mineral interactions;
3. gender-specific (female and male) vitamin and mineral requirements;
4. time-related dosage, that is, morning (AM) and evening (PM) dosages;
5. the composition of the formulation which includes add-on modular formulations that addresses additional nutrient requirements for those under physical and/or mental stress; and
6. reducing the risk of coronary heart disease and stroke because of a modular add-on module containing aspirin, designed to optimize the benefits of aspirin when taken with the vitamin formulation.

The Module 1 formulation also allows the use of aspirin without interference by excessive dosages of nutrients which may contribute to decreased blood clotting, such as vitamin E. In addition, the Modular 1 composition contains appropriate levels of folic acid, vitamin B12 and vitamin B6 which reduce homocysteine levels that increase the risk of coronary heart disease.

The assessment of nutritional status is complex and requires many expensive laboratory determinations as previously cited. Thus, it is not possible or practical to screen every person, nor indeed even all those in whom a vitamin and mineral deficiency is suspected. Therefore, the Module 1 formulation is useful in providing a scientifically designed modular formulation that will help insure that an individual's intake that meets the Recommended Dietary Allowance, with additional levels of specific nutrients which contribute towards the reduction of diseases. See Nutrition Checklist, The Nutrition Screening Initiative, 2626 Pennsylvania Ave, NW, Suite 301 Washington, D.C. 20037. Moreover a multiple micronutrient supplement can be indicated to help replace nutrients depleted by smoking, alcohol, antacids, menstruation, oral contraceptives, chronic illness, physical or emotional stress, surgery, exercise, and dieting.

The Module 1 formulation is based on the concept that increasing the dosage of one nutrient, may affect the absorption or utilization of another vitamin or mineral. For example, one function of vitamin C is to facilitate iron absorption, Fairbanks, V. S., Iron in medicine and nutrition, in Shils, E. M., et al Modern Nutrition in Health and Disease, eighth edition, Chapter 9, Lea and Febiger, 1994; vitamin D is essential for calcium absorption, Reynolds, J. et al.,: The Role of Vitamin D Metabolites In Bone Resorption. Calcification Tissue Res. 12:295–301, 1973; Vitamin A and E metabolically interact.

Moreover, the dosage of one nutrient, if not physiologically appropriate, may change the requirement of another nutrient and even impair immune responses. For example, while physiological doses of zinc is required for immune competency, excessive zinc actually hinders the immune system. See Chandra, R. K Excessive Intake of Zinc Impairs Immune Responses, JAMA 1984; 252:1443–6. High levels of vitamin E and D decrease the activation of interleukin 2; thus, the formulations of the present invention do not use megadoses of any vitamins or minerals.

This unique invention provides a modular supplement with all essential nutrients needed for the development and support of immune function including the B-vitamins, vitamins A, C, E, D and beta carotene, and appropriate levels of minerals such as selenium, magnesium, copper, iron, calcium and manganese. See King, J. C. and Keen, C. L. Chapter on zinc, in Shils, E. M., et al Modern Nutrition in Health and Disease, eighth edition, Chapter 10, Lea and Febiger, 1994.

The module formulations provide nutrients in appropriate amounts at morning and evening meals to achieve the benefit of maximum absorption. The two-dosage per day system allows enhanced absorption of nutrients. The AM and PM dosages allow greater absorption of the water soluble vitamins (B-complex and C) which are not readily stored by the body. The AM tablet provides micronutrients required for energy-producing reactions when physical and mental activity is greater at the start of, and throughout the day. The PM dosage contains a substantial amount of the fat soluble vitamins at a time when the fat content of the evening meal is relatively high, thus facilitating the absorption of fat-soluble vitamins.

The module formulations can also be helpful in persons suffering with illnesses whose diagnoses has been established and whose eating patterns do not supply essential micronutrients. Most diseases induce greater vitamin and mineral requirements due to fever, the need for the immune system to respond with greater numbers of white cells, especially polymorphonuclear leukocytes and lymphocytes, and increased protein synthesis for the generation of the various immune globulins and other blood moieties during infectious and other disease processes. The Module 1 formulation also may be useful in the management of diabetes, gum disease, osteoporosis, certain gastrointestinal malabsorption conditions in adults and elderly, and recovery from surgery or trauma involving burns, fractures; or tissue damage requiring wound healing, in infectious diseases and immune disorders.

The Module 1 formulation is unique in that it also provides a Module stress formula to be taken when higher dosages are indicated. This additional Module 2 formulation contains higher levels of the B vitamins, magnesium, calcium, beta carotene and other nutrients involved in stress-mediating reactions. It is recognized that psychological or emotional stress is related to coronary heart disease, eating pattern disorders, various psychosomatic syndromes, hypertension, mucous colitis & other gastrointestinal diseases.

Module 2, see Tables II and III, is an add-on stress Module which provides the nutrients required for immune competency. As previously emphasized, nutritional status must be adequate to assure proper immune functions. Many persons, especially the elderly are at risk for low intakes of vitamins C, E, B6, and zinc in their diet. The stress Module 2 increases the levels supplied of these nutrients.

Lifestyle factors such as smoking, strenuous exercise, dieting, use of certain medications, and oxidative stresses due to environmental toxins and natural metabolic processes occurring in man and animals may contribute to nutritional deficiencies. Some studies have ascertained that immune function and general health appears to improve for many older people taking a multiple vitamin-mineral supplement. See Meydani, S. N. Nutrition Reviews Vol. 51, No. 4 April 1993 PP 106–115. Risk of infection in the elderly was also decreased when a multivitamin preparation was taken daily. See Chandra, R. K. Effect of Vitamin and Trace-element Supplementation on Immune Responses and Infection in Elderly Subjects the Elderly, Lancet 1992; 340:1124–27. Vitamin B6 deficiency impairs interleukin 2 production and lymphocyte proliferation in elderly adults and is reversible by vitamin B6 repletion. See Meydani, S. N., et al AJCN 53(5):1275–80, May 1991. The basic Module 1 formulation provides these nutrients while the add-on stress Module 2 provides higher levels.

Modules 1, 2 and 3 provide a natural form of vitamin E (d-alpha tocopherol) which is 36% more active than a less expensive synthetic vitamin E (dl-alpha tocoperol) used in many formulas. This may be especially important for people at risk for recurrent infections. See Malkowska-Zwierz, et al, Archivum Immunologiae et Therapiae Experimentalis 39 (1–2):109–15, 1991.

The immune enhancing effect of vitamin E may be related to decreased lipid peroxidation products which occurs with vitamin E supplementation. See Meydani, S. N., Am J. Clin. Nutr. 53(4): 984, April 1991. The mineral selenium is crucial to the body's natural antioxidant enzyme system and works synergistically with vitamin E, both contributing to the maintenance of total immune system defenses. See Dhur, A., et al Comp. Biochem Physiol. 96C (2): 271–80, 1990.

Vitamin A in the formulas of the present invention modulate B-cell functions. See Blomhoff, H. R. et al. Vitamin A is a Key Regulator for Cell Growth, Cytokine Production, and Differentiation in Normal B Cells, Journal of Biological Chemistry 267(33):23988–92, Nov. 25, 1992. Retinols are also a major factor in T-cell activation, Garbe, A. et at. Retinoids are Important Cofactors in T-Cell Activation, J. of Experimental Medicine 176 (1):109–17, Jul. 1, 1992, and for human B cell functions. See Buck et al. Retinol is essential for growth of activated human B cells. J. of Experimental Medicine 171 (5):1613–24, May 1, 1990. The add-on stress Modular 2 formulation also provides higher levels of beta-carotene as it has significant effects on the immune system, Prabhala, R. H., et al., Cancer 67(6) 1556–60 (1991), which are not yet fully identified. Vitamin D also plays a role in immune competency, Porsova-Dutoit, et al, Studies on the Immunomodulatory effects of Vitamin D. Endocrine Regulations 27(2):75–82, June 1993, and can induce human monocyte to macrophage maturation, Kreutz, M. et al. Blood. 76(12):2457–61 Dec. 15, 1990 which is essential for the destruction of infectious agents. Although clinical scurvy due to vitamin deficiency is seldom seen in young and middle age adults, it occurs in the elderly, specially those in nursing homes. Vitamin C deficiency can result in oxidative changes when it is 50% of baseline values in plasma leukocytes. See Jacob, R.A. et al. Immunocompetence and Oxidant Defense during Ascorbate Depletion of Healthy Men. AJCN 54 (6 Suppl):1302S–1309S, 1991. Young women supplemented with zinc and vitamin A exhibited higher proliferative responses of T lymphocytes on allergen challenge. It is therefore believed that zinc and vitamin A intake could result in health benefits for persons with suboptimal vitamin and mineral intake. See Kramer, T. R, et al. Lymphocyte Responsiveness of Children Supplemented With Vitamin A and Zinc. AJCN 58(4):566–70, October 1993. Smokers require more vitamin C to maintain adequate plasma levels of this important antioxidant vitamin. The Modular 2 formulation provides 5 times the RDA for vitamin C, with higher amounts in the Stress formula to compensate for the added loses due to smoking.

Module 2 also supplies higher levels of specific nutrients required for healing. Clinical nutritionists and surgeons have long recognized that nutritional status is a major contributing factor for post-operative healing and the prevention of post-surgical complications. Prior nutritional status, associated disease, calorie intake, protein intake (including desirable ratio of essential to non-essential amino acids), and the micronutrients vitamins A, C, E, B1, B2, zinc and iron, all contribute to the healing process. For example, vitamin C is required for collagen synthesis, vitamin A for tissue epithelization, and zinc for cellular mitosis and proliferation and as a cofactor in many protein synthesizing enzymes. See Trujillo, E. B. Effects of nutritional status on wound healing. J. Vasc. Nursing 11 (1): 12-8 March 1993. Low serum concentration of vitamin C was considered the key contributing factor in bed sore development in elderly patients who sustained femoral neck fracture. See Goode, H. F., Burns, E. Walker BE. Vitamin C Depletion and Pressure Sores in Elderly Patients With Femoral Neck Fracture, BMJ 305 (6859):925–7, Oct. 17, 1992. In patients with serious blunt trauma, neutropil locomotor dysfunction is partly the result of auto-oxidation, evidenced by low serum and cellular vitamin C and E. In patients receiving antioxidants, neutrophil function was shown to be significantly improved. See Maderazo, E. G. et al. A randomized trial of replacement antioxidant vitamin therapy for neutrophil locomotory dysfunction in blunt trauma. J. of Trauma, 31(8):1142–50, August 1991, Verix Vitamin E Information Service. Post-operative oral multivitamin supplementation in a study of 140 patients also was found to be useful in correcting folate and B12 anemias following gastric bypass surgery. See Brolin, R E., Gorman, R. C., Milgrim, L. M., Kenler, H. A. Multivitamin prophylaxis in prevention of post-gastric bypass vitamin and mineral deficiencies. Inter. J of Obesity, 15(10):661–7, October 1991. Burned patients exhibit elevated levels of plasma lipid peroxidation products and reduced levels of serum vitamin E and total sulfhydryl group concentration. Increased oxygen free radical activity and activation of white blood cells and macrophages was also demonstrated. See Nguyen, T. T. Cox CS. Traber DL Gasser H. Redl H. Schlag G. Herndon DN. Free radical activity and loss of plasma antioxidants, Vitamin E and sulfhydryl groups in patients with burns: the 1993 Moyer Award. J. Burn Care Rehabil. 14(6):602–9, November–December 1993.

Module 2 also supplies nutrients mediating fatigue and emotional stress. Fatigue can be a symptom of many diseases, and the specific diseases must be diagnosed before any vitamin and mineral supplement is consumed. However, it is known that fatigue is a major symptom in deficiencies of calories, proteins and specific vitamins and minerals. A classical example from clinical nutrition is the fatigue associated with some of the vitamin and mineral deficiency causes of anemia. These include iron, folate, and B12 deficiency anemias. However, it is not generally recognized that deficiencies of vitamins B1, B2, B6, C, E, A, and the minerals, zinc and magnesium can also cause anemia. These nutrients are supplied within this invention with higher levels provided in the stress module. The basis for anemias involve the profound role vitamins and minerals play in metabolic energy-yielding and cellular metabolic reactions required by everyday activities. Micronutrients also have critical metabolic roles in the body's synthesis of hormones, neurotransmitters, enzymes and many other compounds and reactions that occur every second in order to provide a sense of physical and psychological well being, the lack of which may result in fatigue. Vitamins are not oxidized to yield energy; however the micronutrients in the formulation are essential for the body's metabolic reactions involving the conversion of food into energy.

Many adults do not get adequate levels of calcium in their diet; specifically, the average daily intake for American women was 450–550 mg daily, or slightly above one-half of the RDA of 800 mg. See National Institute of Health (1984) Statement of the Consensus Development Conference on Osteoporosis. DHAHS, Public. # (PHS) 1984-421-132: 4652 U.S. Govt. Printing Office, Washington D.C.; and Optimum Calcium Intake NIH Consensus Statement, Jun. 6–8, 1994; 12(4):1–31 US Govt. Printing Office, Washington, D.C. The NIH Conference Statement of 1994 indicates an optimal intake of 1,000 mg daily for women age 24 to 64 and 1500 for age 65 and over. For women especially, this may increase their risk of developing osteoporosis due in part to decreased estrogen levels as they increase in age. The Module 1 formula for men or women provides over 500 mg of calcium with 100% of the RDA for vitamin D. An individual consuming two servings of milk products daily could have a sufficient intake. However, post-menopausal women who are not taking estrogen, and those who have had hysterectomies may require higher intakes of calcium. An additional 450 mg of calcium is provided in the add-on stress Module 2 for these individuals along with additional magnesium, copper, and manganese to enhance the absorption of calcium.

These examples illustrate some of the beneficial ways in which Module 1 in this invention relieve fatigue, enhance the body's natural defenses, aid healing and recovery, and reduce the risk of osteoporosis.

Module 3 is a specific formula to address the nutritional aspects of Syndrome X. See Tables II and III. Syndrome X has been described in the last decade relating to a constellation of significant abnormalities which increase the risk of diabetes, hypertension, hyperlipidemia, hyperinsulinemia and obesity which create risk factors for atherogenesis and coronary heart disease.

Chromium is utilized within this invention in all of the modules to help maintain normal glucose metabolism. As an essential cofactor for insulin, it is involved in mediating normal blood sugar and insulin functions. Chromium deficiency results in impaired glucose tolerance in animal and man, and is corrected when dietary chromium reaches normal levels. Human studies indicate that chromium can correct mild diabetes and glucose intolerance in some persons. See Offenbacker, E. G., et al., Diabetes 29: 919–25 1980 Beneficial Effects of Cr-rich Yeast on glucose Tolerance and Blood Lipids in Elderly Subjects. Another major function of chromium is the lowering of plasma insulin levels. Many studies document elevated insulin levels as a basis of "Syndrome X," which is clinically manifested by obesity, hyperglycemia, insulin resistance, hyperinsulinemia, hypertension and enhanced atherogenesis. The possibility of correcting hyperinsulinemia may be of substantial public health importance. As is well known, obesity associated with hyperinsulinemia may play a role in the pathogenesis of diabetes, hypertension, atherosclerosis and coronary heart disease.

The present invention also considers the nutritional aspects of aging and longevity. The free radical theory of aging and its role in disease causation has opened a new, major research epoch in clinical nutrition and medicine. Free radical damage is now recognized as simply a fact of physiological life. Every breath of oxygen a person inhales is inducing free radical formation which is inherently injurious to subcellular membrane architecture modules, including nucleoli, mitochondria and lysosomes which sustain life itself. Atomic and molecular DNA damage induces mutations and cytotoxic effects within cells, which is a new and basic pathogenic pathway towards increasing the risk of coronary heart disease and cancer.

In order to limit the significant negative impact of free radicals, many organ cells utilize inherent available cytological and immune defenses. These include oxidative DNA repair, which is the role of polyADP-ribosylation, serving to rejoin DNA strand breaks; and the endogenous antioxidant compounds ubiquitously found in the body, such as uric acid, are also protective. Dietary compounds such as vitamins (A, C, E) beta carotene, alpha carotene, lycopene, lutein, riboflavin, and minerals such as selenium and zinc are all part of the Module 1 formulation and the stress Module formulation to augment the body's natural defenses against free radical damage.

The novel AM/PM dosage regimen embodied in this invention maintains higher levels of antioxidants in the tissues than ordinary vitamins taken once daily since water soluble antioxidants such as vitamin C and the B vitamins are utilized and need to be replaced throughout the day.

As people age, their nutritional status continues to change, often in a direction that may accelerate the aging process. Early aging as well as chronic geriatric disease foreshortens life, but both can be prevented to some extent by the control of their nutritionally determined risk factors.

It has been shown above that lack of host resistance increases the risk of cancer. Vitamins A, B6, C, and E and the minerals selenium and zinc, in dosages provided in the Module 1 and add-on formulations, contribute to the restoration and maintenance of immunocompetence, which could benefit consumers in decreasing cancer risk. An additional major function of antioxidants is to also confer protection against some degenerative diseases associated with older persons.

In accordance with Module 4, this novel multivitamin, mineral and antioxidant formulation is specifically designed to include aspirin, or plants rich in salicylic acid such as willow bark and queen meadow within its formula or as an add-on module. See Tables II and III. The micronutrient dosages and precise combinations in the formula function independently, or synergistically with aspirin to provide definitive health advantages.

Specific antioxidant micronutrients such as vitamins E, C, beta-carotene, selenium, copper, manganese, magnesium, folic acid, vitamin B6, and vitamin B12 and other nutritional compounds formulated into the invention enhance aspirin's ability to reduce risk of coronary heart disease and certain cancers. The Module 4 formula has excluded nutrients which can interfere with aspirin's benefits, such as vitamin K.

The Physician's Health Study, a randomized, double-blind placebo-controlled trial conducted by Harvard Medical School faculty demonstrated a conclusive reduction in myocardial infarction in persons 50 and over by the use of 325 mg of aspirin every other day. There were 139 myocardial infarctions among those assigned to aspirin and 239 among placebo subjects. This represents a 44 percent reduction in risk. The benefits of aspirin were significant for both fatal and non-fatal myocardial infarctions. See Final Report on the Aspirin Component of the Ongoing Physician's Health Study, New england Journa l of Medicine. Jul. 20, 1989 321 (3) pp. 129–135.

This led the FDA to allow the use of aspirin for the treatment of patients with a previous myocardial infarction or unstable angina. A review of 25 randomized studies of anti-platelet therapy in patients with a history of cardiovascular disease demonstrated a 25 percent reduction in the incidence of subsequent significant vascular events (nonfatal myocardial infarction, nonfatal stroke, or death from cardiovascular disease), a 32 percent decrease in nonfatal myocardial infarction, a 27 percent reduction in nonfatal stroke, and a 15 percent reduction in cardiovascular mortality. It is presumed that much of the physiological benefits associated with aspirin are due to its ability to decrease blood clotting through decreased platelet agglutination.

The above evidence justifies the use of aspirin by selected persons on a daily basis as a preventive agent. Many of these consumers also take multivitamins which may interfere with aspirin's benefits. For example, many multivitamin preparations contain vitamin K. One popular brand is designed for older individuals and contains 80 mcg of vitamin K. This is the same segment of the population (55 years and older) which showed the greatest benefit from aspirin use in the Physician's Health Study.

The presence of certain compounds, such as vitamin K, in commonly sold multivitamin formulations may negate the full benefits of aspirin for some individuals. Recent data suggest that aspirin significantly delays and inhibits thrombin generation in whole blood.

Women taking oral contraceptives are at increased risk of incidences of thromboses. Oral contraceptives may increase serum vitamin K-dependent clotting factors as well as other clotting factors. See Horton, M. D, et al in Exercise, Nutrition and Energy metabolism, 1988 Editors, Chapter 14 Drug Nutrient Interactions by Kendrick, Z. V., et al.

Administration of various multi-vitamins and nutritional supplements with aspirin may induce risks. It is known that aspirin taken with omega-3 fatty acid supplementation in humans prolongs bleeding time and that vitamin E with aspirin reduces the concentration of vitamin E needed to inhibit platelet aggregation. See Violi, et al, Atherosclerosis 82:247–252, 1990.

It has been shown in animal models that taking ascorbic acid or acetylsalicylic acid alone did not simulate or inhibit the production of interleukin-6 whereas a combination of both substances caused a significant stimulation. See Hockertz, S., et al. Effect of acetylsalicylic acid, ascorbate, and ibuprofen on the macrophage system. Arzneimittel-Forschung. 42:1062–8, August 1992.

The bioflavonoid quercetin scavenges the superoxide anion radical directly and inhibits cyclooxygenase as does aspirin. See Gu Zhen-Lun et al., Acta pharmacologica Sinica. 14(3):263–5, May 1993.

Serious gastrointestinal, cerebrovascular or renal bleeding can occur from all dose levels of aspirin intake. The formulation avoids high levels of vitamin E and fish oil found in some vitamin preparations that may produce excessive bleeding when combined with aspirin.

Our study data (see following) suggests that there are no apparent micronutrients in this invention which deter the effectiveness of aspirin to play its physiologic and metabolic role as a significantly effective anti-platelet agglutinating agent at the dosage we used. Furthermore the formula may be more effective than multi-vitamins due to the inclusion of nutrients which enhance aspirin's benefits and the avoidance of nutrients which may interfere with aspirin's benefits such as vitamin K.

The incidence of myocardial infarction peaks at 10 AM in the morning for men. Thus, the taking of the AM micronutrient antioxidant formulation containing aspirin may play a preventive role in reducing myocardial infarction incidence. The AM and PM micronutrient formula dosage schedule with the add-on aspirin module is a novel formulation which can be of substantial public health and clinical usefulness. The modular add-on system uniquely designed in this invention allows the physician or consumer to tailor a vitamin program to address individual concerns and allows the physiologic functions of aspirin to be enhanced.

The AM/PM formulation, add-on stress Module 2 and aspirin Module 4 are unique as they contain original dosage levels of nutrients that provide definitive health advantages individually or synergistically. Vitamin C protects the duodenum against aspirin-induced duodenal injury and bleeding. See McAlindon, M. E. et al Effect of allopurinol, sulphasalazine, and vitamin C on aspirin induced gastroduoderal injury in human volunteers, Gut, 38(4), 1996, p.518–24. Antioxidant vitamins such a C, and E, plus aspirin can help reduce the risk of coronary heart disease in women. See Hennekens, C. H, Platelet inhititors and antioxidant vitamins in cardiovascular disease, AM. Heart J, December 1994, 128 (6pt2) p1333–6. Vitamin D binding protein plus gelsolin can decrease actin-induced platelet agglutination. See Vasconcellos, C. A; Lind, SE, Coordinated inhibition of actin-induced platelet aggregation by plasma gelsolin and vitamin D-binding protein, Blood, Dec. 15, 1993, 82 (12) p. 3648–57. Aspirin is bound to protein in human serum. Those vitamins and minerals that are related to protein metabolism necessarily play a role in optimizing aspirin metabolism. These include vitamin B6, folate, vitamin B12, C, and various minerals and trace minerals which are enzyme cofactors. See Lee, S., et al, Protein binding of acetylsalicylic acid and salicylic acid in porcine and human serum. Vet. Hum. Toxical, June, 1995, 37(3) p. 224–5. Aspirin stimulates the immune system by increasing interleukin and interferon production, and by stimulating human lymphocyte proliferation. Vitamins such as A, E, folate, B12, and minerals such as iron, zinc, selenium and other micronutrients are required for the synthesis of immunity-related compounds. See Lotzerich, H., et al, Influence of acetylsalicylic acid on antibody-dependent cellular cytotoxicity (ADCC) of peritoneal macrophages, Anticancer Res. January–February 1993, 13, (1) p.87–92; and Brouard, C. et al., Modulation of rat and human lymphocyte function by n-6 and n-3 polyunsaturated fatty acids and acetylsalicylic acid. Ann Nutri. Metab. 1993, 37 (3) p.146–59. Vitamin E is required for the oxidation of long chain polyunsaturated fatty acids at the mitochondrial membranes, such as eicosanoids, the synthesis of which are stimulated by aspirin, Claria, J., Serhan C.N. Aspirin triggers previously undescribed bioactive eicosanoids by human endothelial cell leukocyte interactions, Proc. Nat'l Acad Sci, Oct. 10, 1995, 92(21) p.9475–9, aspirin is now being considered as a free radical scavenger. Therefore, vitamins such as A and E, which "protect" each other's anti-oxidative potential, may also interrelate with and enhance the benefits of these micronutrients. See Kuhn, W., et al, Acetylsalicylic acid as free radical scavenger: An argument for increased dosages in acute and preventative therapy of vascular diseases, Fortschr Med., Nov. 30, 1995, 113(33). p.483–4.

The above indicates the synergistic interrelationships which exist between vitamins, minerals and aspirin, which are reflected in the novel Modular 1 formulation with its modular add-on components and potential for reducing disease and promoting health and longevity.

The Module 4 component of the present invention includes aspirin in one of the following exemplary dosages:

(1) aspirin about 30 mg;
(2) aspirin about 55 mg;
(3) aspirin about 81 mg; or
(4) aspirin about 200 mg.

Each of these four dosage variations of Module 4 may be taken with Module 1, 2, and either the low or the high dose variation of Module 3.

EXAMPLE #1

Anti-platelet agglutinating response of aspirin given at the same time with a Module 1 multivitamin and mineral formulation is studied.

This study of 7 healthy subjects, four female and three males, suggests that low dose aspirin (81 mg) taken daily, for 7 days simultaneously with the AM dosage of our novel formulation, is capable of inducing significantly increased bleeding times compatible with the effects documented to reduce coronary heart disease risk.

Bleeding times are done before and after the 7 day experimental period. A standard method of determining the bleeding time is utilized (Surgicutt). Dietary histories are obtained daily from the study subjects, to assure that their usual eating patterns are maintained, and that excessive deep green vegetables are not consumed which might influence the bleeding times of the subjects. This is done because recent studies imply that aspirin may affect fibrinogen and clot characteristics, and thus influence the results. Prothrombin times are also done and do not change significantly from baseline values in all subjects.

Group One consisted of 2 males and 2 females who take the Module 1 AM/PM formula plus 81 mg of aspirin from Module 4. The two nonsmokers increase their bleeding times from their respective baseline values by two minutes in one subject and to over 15 minutes in the other. By contrast, the two smokers show a decrease in bleeding time of 4.5 minutes in one subject, and a decrease of 1 minute in the other.

Group Two consists of 2 females (one smoker) and 1 male who also take 81 mg of aspirin with a commercially available multivitamin (with 80 mcg of vitamin K) plus 81 mg of aspirin. One nonsmoker increases her bleeding time to over 15 minutes. Of the two other subjects, one non smoker decreases his bleeding time by 3.5 minutes, while the smoker decreases her bleeding time by two minutes.

Of the three smokers in both groups, all three show a decrease in bleeding time averaging 2.5 minutes.

Of the seven subjects, 4 are non-smokers and 3 smokers. Three of the 4 non-smokers show definite increases in the bleeding times after 7 days on the Module 1 formulation and aspirin. All 3 smokers and 1 non-smoker show a decrease in bleeding time. The impact of smoking on bleeding time is unexpected, and warrants further study.

These results are consistent with the findings which indicate that study populations exhibit a variable response to aspirin. The data further supports the effectiveness of the inventor's formulation taken with, or containing an 81 mg aspirin module.

TABLE 1

EFFECT OF INVENTOR'S MODULAR FORMULA AND ANOTHER MULTI-VITAMIN WITH VITAMIN K. ON BLEEDING TIMES

| SUBJECTS | Bleeding Time (minutes) | |
| --- | --- | --- |
| | Baseline | Post Aspirin |
| GROUP 1 Module 1 + Aspirin (81 mg) | | |
| Nonsmokers | | |
| JJ (F) | 4.0 | 6.0 |
| GC (M) | 6.5 | >15. |
| Smokers | | |
| TB (M) | 7.5 | 3.0 |
| CF (F) | 6.0 | 5.0 |
| GROUP 2 Commercially available multivitmin containing Vitamin K+ Aspirin (81 mg) | | |
| Nonsmokers | | |
| DM (F) | 5.5 | >15. |

TABLE 1-continued

EFFECT OF INVENTOR'S MODULAR FORMULA AND ANOTHER MULTI-VITAMIN WITH VITAMIN K. ON BLEEDING TIMES

| SUBJECTS | Bleeding Time (minutes) | |
| --- | --- | --- |
| | Baseline | Post Aspirin |
| GP (M) Smokers | 5.5 | 2.0 |
| DC (F) | 6.0 | 4.0 |

Potential enhancement or potentiation of low dose aspirin may occur by the action of another micronutrient in the modular formulations, such as vitamins B6, or vitamin C, or vitamin E by the special way the formula is taken in the AM and PM; or in the addition of the stress module which may also be taken twice daily.

The formulation embodied in this invention with the modular add-on stress, coronary heart disease and aspirin modules represents a novel approach to supplementation with unique merits and health advantages.

EXAMPLE #2

A telephone survey is conducted of 983 persons taking Module 1 formula for a period for at least about 90 days. About 76% of the subjects experience improvement in their health status; about 65% report more energy, vitality and stamina; about 61% report fewer colds; about 27% cite greater mental alertness. Of the 7% of the subjects who are airline or private pilots, about 91 % stated that they feel more alert while taking the formula. This response suggests that the Module 1 formula exerts a sense of physical well-being.

The Module 1 formula modified for men and women, or taken alone, or with the stress Module 2, taken alone or with the coronary heart disease (CHD) Module 3, or taken alone, or with the aspirin Module 4 are believed to be examples of best mode for use of this invention. Separately, Module 5 may be taken alone, or Module 6 may be taken alone, or Module 7 may be combined with Module 1 and/or 2 and/or 3. This represents at the present time, with possible minor modifications of dosages, or minor additions or deletions in the incremented dosages, or sources of nutrients, various best mode of this invention.

The use of the Module 1 formation separated into AM and PM tablets are to be taken with meals on a daily basis. The formulations contain no vitamin K to prevent interference with aspirin's effects. The formulas may contain vitamin C to help heal aspirin-induced gastric irritation. The antioxidant lycopene has been added to protect the antioxidant function of vitamin C and other antioxidants. The formulas contain no citrates, acetates or phosphates which can react with aspirin to produce potentially toxic compounds. The formulas avoid excessive beta carotene which may negatively affect the activity of alpha-tocopherol (vitamin E). This effect has been taken into account in the formulations by providing appropriate doses. The formulas utilize water soluble vitamin E which do not require dietary lipids for absorption. The inclusion of coenzyme Q-10, as a facilitator of vitamin E, and a ubiquitous intracellular antioxidant, which has recently been found to preserve myocardial function, is a useful and unique advantage of this formulation. The limitation of excess copper in the formula helps prevent the negative effects of copper which can oppose the antioxidant action of vitamin E. The formulas may also contain capsicum or chili pepper to counteract aspirin's negative effects on prostaglandins. Alternately the aspirin or aspirin-like compounds could be microencapsulated or time released. The combined formulations and the aspirin add-on module are buffered to a non-acidic neutral pH.

The complete modular formulation including all of the modular add-on formulations an individual may take on a daily basis, with modifications will fall within the following dosage range for the following micronutrients as listed below:

| | |
|---|---|
| Vitamin B-1 | about 0.7 to about 15 mg |
| Vitamin B2 | about 0.7 to about 15 mg |
| Vitamin B6 | about 2.0 to about 100 mg |
| Niacin | about 6.0 to about 100 mg |
| Folate | about 50.0 to about 800 mcg |
| Pantothenic Acid | about 4.0 to about 50 mg |
| Vitamin B12 | about 0.5 to about 40 mcg |
| Biotin | about 5.0 to about 300 mcg |
| Calcium | about 100.0 to about 1,500 mg |
| Magnesium | about 25.0 to about 500 mg |
| Iron | about 1.0 to about 20 mg |
| Zinc | about 5.0 to about 30 mg |
| Manganese | about 1.0 to about 10 mg |
| Selenium | about 10.0 to about 200 mcg |
| Chromium | about 10.0 to about 300 mcg |
| Copper | about 0.0 to about 4 mg |
| Coenzyme Q-10 | about 5.0 to about 300 mg |
| Vitamin A | about 200.0 to about 15,000 IU |
| Beta Carotene (Vit. A equivalent) | about 500.0 to about 15,000 IU |
| Alpha Carotene | about 50.0 to about 2,000 mcg |
| Lycopene | about 50.0 to about 10,000 mcg |
| Lutein | about 50.0 to about 5,000 mcg |
| Zeaxanthin | about 5.0 to about 500 mcg |
| Vitamin C | about 20.0 to about 1,000 mg |
| Vitamin D | about 0.0 to about 400 IU |
| Vitamin E | about 5.0 to about 2,000 mg |
| Grape Seed Extract | about 0.0 to about 300 mg |
| Green Tea Extract | about 0.0 to about 500 mg |
| Hawthorne Berry Extract* * (Crataegus Oxyacantha) | about 0.0 to about 500 mg |
| L-Carnitine | about 0.0 to about 700 mg |
| Alpha Lipoic Acid | about 0.0 to about 750 mg |
| Taurine | about 15.0 to about 1,000 mg |
| Quercitin | about 0.0 to about 500 mg |
| Garlic | about 0.0 to about 500 mg |
| Aspirin | about 0.0 to about 500 mg | or its bioequivalent, which may include natural sources of salicylic acid derived plant.

By the term "aspirin," it is meant to include related compounds that are aspirin-like (bioequivalents) or easily converted to aspirin including both man-made and naturally occurring, such as but not limited to helecin, salicin, salicylic acid or other salicilates and esters, their precursors or derivatives, ibuprofen, ketoprofen, etc. Natural sources would include but need not be limited to Salix Alba (White or European Willow), S Nigra (Pussy Willow, S. Caprea, S. Fragilis, S Russilliana, S. Purpurea, S Pentandra, Poplar, Spiroea Ulmaria, Spiraea Salicifolia (Meadow Sweet), and Castor. Obviously, only the desired compounds would be extracted, processed, tested and utilized either as is (bioequivalent) or converted to acetylsalicylic acid (aspirin) by one skilled in the art, or numerous published methods.

The formulas may contain other synergistic dietary or nutritional compounds such as garlic, bioflavinoids, quercetin, capsicum, boron, melatonin & DHEA. The formulas may also contain glycerol, sorbitol, sucrose, magnesium stearate and other excipients and binders. Additional calcium may also be included for sizing and buffering, The Modules of the present invention may be administered as and formulated into tablets, caplets, capsules or other oral dosage forms that do not defeat the objectives of the present invention. An example of a tablet manufacturing process in accordance with the present invention is as follows. Production work orders are generated and issued from a master formula. Examples of a master formula can be found in Tables II and III. Currently, the modular systems of the present invention contain no other ingredients other than those listed in Tables II and III which, subsequent to tableting, are simply coated with an aqueous film consisting of cellulose, chlorophyll, water and titanium dioxide as discussed hereinbelow. These work orders contain information specific to each batch, such as lot #, batch size, date of release and estimated date of shipping. The production process is sequential, beginning with raw material weighing and ending with end product shipping.

Work order batch records are released from order processing and given to the director of Quality Control for review. These are then given to the Operations Manager for review and placement into production scheduling and weigh master review.

Raw material quantities are specified to weighing personnel on the batch record. Each item is weighed individually by the employee assigned to this job. Raw material is then warehouse and weighed in an appropriate container (ie: plastic bag, drum etc.) as determined by amount of material.

Once the material is weighed the batch record is filled out with:

1) The amount of material weighed;
2) The component #;
3) The identification of the action; and
4) The identification of the employee who revalidated that steps #1,2 & 3 were completed.

An inventory adjustment entry is also executed on the inventory control card for each raw material item. Upon completion of the weighing of each raw material, the routing documentation is completed with dates of weighing, number of containers per batch, identification of weighing personnel and remarks pertinent (if any) to this batch. Completed paperwork is forwarded to next department.

The compounding department takes the components of the order and blends them into a homogeneous blend. The material is weighed to verify actual vs. theoretical yield. Any detectable loss is brought to the attention of the Director of Quality Control for action. Upon verification of correct weight, raw material in small amounts is triturated and the granulated material is loaded into an assigned mixer. The non-granulated raw materials are then loaded into the same mixer and blended for a specified amount of time.

Once mixing is complete the entire mixer is downloaded into stainless steel drums and re-weighed to confirm the actual yield. Any detectable deviation is brought to the attention of the Director of Quality Control or his designee. Routing documentation is noted for compounding with the dates of compounding, the mixer used, the results of weighing, the number of containers holding the order and identification of the employees doing the work.

In addition to the ingredients listed on the label, i.e., Tables II or III, it should be understood by those of skill in this art that the oral dosage forms of the present invention may include other components, such as fillers, binders and excipients such as, hydroxypropyl methylcellulose, methacrylic acid copolymer, type C, microcrystalline cellulose, polyethylene glycol, pregelatinized starch, talc, titanium dioxide, triacetin, calcium carbonate, and FD & C colorings.

Material leaving compounding is placed in the tableting department staging area where it remains until the proper compressing machine is available. The batch record defines running specifications and allowable deviation. The machine operator begins a "set-up" to arrive at the target figures. The set-up tablets are taken to the Operation Manager for evaluation and approval. If they meet the technical specifications an approval is given to run the job. A sample is given to the Quality Control Laboratory to check the tablet color, size, hardness, dimensions, thickness and disintegration time. If all the specifications are met, approval would be given to run the machine by the Manager of the Quality Control Lab.

Once the job is running on the tablet machine "in process" quality assurance checks are begun. Every 15 minutes 10 random samples are pulled and checked to insure adherence to set-up specifications. Sample results for weight and thickness are recorded as permanent part of the batch record. Samples tablets are taken routinely during the run to the laboratory for quality control validation relating to disintegration, hardness and weight variation. Continuation of the run is dependent upon satisfactory laboratory results.

Once the order has been tableted, a composite sample which had been intermittently selected from the run, is submitted to the Analytical Laboratory as a retained FDA sample and for routine analytical testing. Compressing department routing information is recorded once the run is complete. This relates to the number of boxes into which the batch went, the tablet machine used, the date of tabletting and identification of the production personnel operating the equipment.

Once the Director of Quality Control and Analytical Laboratory have approved the uncoated tablets for release to coating, they are moved into the coating staging area. The tablets are loaded into an aqueous based coating system. The operator sets the temperature, nozzle velocity and pan speed as dictated by tablet size and the coating solution which is specified; on the work order. This solution consists of water, cellulose, schlorophyll and titanium dioxide. The tablets are rotated in the pan to remove any dust. The spray system is then activated and any nozzle adjustments are made as necessary. The spray is constant taking between 120 minutes or longer. Constant monitoring is needed to assure a uniform and even coating application. When the coating function is complete, samples are again given to the Analytical Laboratory for evaluation based on standards of uniformity of coverage and texture.

The batch record of the finished product is turned into the Analytical Laboratory with the coated tablet sample for final evaluation. All production department routing checks to include in process inspections are included.

When the Quality Control Analytical Laboratory has determined that all documents are in order and that all quality control requirements, physical and chemical, have been met, the batch record is "released" to shipping by the Director of Quality Control.

A certificate of Analysis is prepared based on the results of the chemical analysis performed and physical checks. An expiration date is assigned based on accelerated shelf life testing done earlier on this product, and signed by the Director of Quality Control Assurance.

The shipping department counts the number of tablets in each box. The average weight of 500 randomly selected tablets is used to set scale. Quality assurance personnel check the tablets for any noticeable defects and recommends either shipping or belt inspection of the tablets for zero defects. Final approval to ship is given by the Director of Quality Control. A separate bulk label is made for each box which identifies the products by lot number and label number, and also supplies the number of the tablets per box. The expiration date as assigned by the Analytical Laboratory and the total number of boxes comprising the order. The completed order is then ready for shipment.

An example of a tablet manufacturing procedure is as follows. Weigh all materials called for on batch record. Inspect all raw materials for uniformity, contaminants and quality control release sticker. Confirm raw material and check expiration date. Label and place in well covered containers prior to compounding to prevent cross contamination. Grind through an oscillator or Fritzmill. Place granulation into a stainless steel drum. Seal immediately and label. Ensure that all outer containers are dust free before opening. Inspect thoroughly and match lot numbers. Obtain a net weight on the material from grinding. Tumble blend until uniform. Label new containers. Set up the tablet press and check for color, size and weight deviation. Take in-process sample to lab for approval including hardness and friability. Compress to established specifications and label containers. Evaluate physical characteristics and chemical potency to meet specifications. confirm lab approval before placing in coating pans. Spray tablets with required coating mix until complete and uniform. Continue rotating pans until dry. Send samples to lab to verify tablets meet all specifications. After laboratory release place tablets into doubled plastic lined containers, seal with tamper evident tags and label. All containers must have pre-approved labels with all information included. Entire area is inspected to have only proper components, labels and tablets for this lot number to be packed. No other materials are present. Machine is set to fill proper count. Tablets are packed, labeled, coded, and jars sealed. Jars are counted and packed into proper boxes and labeled for shipment.

Reference to a manufacturing procedure for an enteric coated module aspirin dosage form in accordance with the present invention is as follows. Blend aspirin and excipients. Compress blend to tablet specifications. Prepare subcoat solution in a stainless steel container. Spray subcoat solution onto tablet core in a 60 inch Accela-Cota. Prepare enteric coating solution in a stainless steel container. Spray enteric coating solution onto tablet cores in a 60 inch Accela-Cota. Prepare color coating solution in a stainless steel container. And then, spray color coating solution on to tablet cores in a 60 inch Accela-Cota.

TABLE II

| Men's Formulation | MODULE 1 | MODULE 2 | MODULE 3 | MODULE 4 | MODULE 5 | MODULE 6 | MODULE 7 |
|---|---|---|---|---|---|---|---|
| Aspirin (or bioequivalents) | | | | 30 mg / 55 mg / 81 mg / 200 mg | same as Module #1 plus 20 mg. of aspirin (or its bioequivalents) within the AM formula's composition. | same as Module #1 plus 81 mg. of aspirin (or its bioequivalents) within the AM formula's composition. | same as Module #3 (Low Dose Formulation), plus 81 mg. of aspirin (or its bioequivalents) included within the composition. |
| Carotenoid Complex | | | | | | | |
| Beta Carotene | 1250 IU | 2500 IU | 1250 IU | | | | |
| Alpha Carotene | 250 IU | 500 IU | 250 IU | | | | |
| Lutein | 400 mcg | 400 mcg | 50 mcg | | | | |
| Lycopene | 400 mcg | 400 mcg | 1000 mcg | | | | |
| Zeaxanthin | 20 mcg | 20 mcg | 50 mcg | | | | |
| Vitamin A | 3,000 IU | 1,500 IU | 200 IU | | | | |
| Vitamin B1 (Thiamine HCl) | 5 mg | 7.5 mg | 1 mg | | | | |
| Vitamin B2 (Riboflavin) | 5 mg | 12.5 mg | 1 mg | | | | |
| Niacinamide | 33 mg | 40 mg | | | | | |
| Pantothenic Acid (d-Calcium Pantothenate) | 15 mg | 10 mg | 2 mg | | | | |
| Vitamin B6 (Pyridoxine HCl) | 5 mg | 15 mg | 2 mg | | | | |
| Biotin | 5 mg | 300 mcg | 6 mg | | | | |
| Folic Acid | 150 mcg | — | 200 mcg | | | | |
| Vitamin B12 (Cobalamin) | 300 mcg | 100 mcg | | | | | |
| Vitamin C* (Buffered Calcium Ascorbate, Ascorbic Acid and Ascorbyl Palmitate) | 6 mg | 6 mcg | 6 mcg | | | | |
| | 150 mg | 600 mg | 200 mg | | | | |
| Vitamin D3 (Cholecalciferol) | 300 IU | 30 IU | 200 IU | | | | |
| Vitamin E (d-alpha Tocopheryl Succinate) | 60 IU | 100 IU | 100 IU | | | | |
| Calcium (Carbonate, Ascorbate) | 225 mg | 450 mg | | | | | |
| Chromium | 80 mcg | 70 mcg | 15 mcg | | | | |
| Copper (Gluconate) | 0.5 mg | 0.5 mg | | | | | |
| Iron (Ferrous Fumarate) | 8 mg | 3 mg | | | | | |
| Magnesium (Oxide) | 100 mg | 200 mg | 25 mg | | | | |
| Manganese (Gluconate) | 4 mg | 1 mg | | | | | |
| Selenium (L-Selenomethionine) | 25 mcg | — | 50 mg | | | | |
| Zinc (Sulfate and Gluconate) | 10 mg | 50 mcg | 20 mcg | | | | |
| Odorless Garlic | 25 mg | 7 mg | 40 mcg | | | | |
| Coenzyme Q-10 | | — | 100 mg | | | | |
| L-Carnitine | | | 200 mg | | | | |
| Grape Seed Extract | | | 50 mg | | | | |
| Green Tea Extract | | | 50 mg | | | | |
| Quercetin | | | 200 mg | | | | |
| Hawthorne Berries* (Flavones) | | 2 mg | 5 mg | | | | |
| Alpha Lipoic Acid | | 30 mg | 100 mg | | | | |

TABLE III

| Women's Formulation | MODULE 1 | MODULE 2 | MODULE 3 | MODULE 4 | MODULE 5 | MODULE 6 | MODULE 7 |
|---|---|---|---|---|---|---|---|
| Aspirin (or bioequivalents) | | | | 30 mg  55 mg  81 mg  200 mg | same as Module #1 plus 20 mg. of aspirin (or its bioequivalents) within the AM formula's composition. | same as Module #1 plus 81 mg. of aspirin (or its bioequivalents) within the AM formula's composition. | same as Module #3 (Low Dose Formulation), plus 81 mg. of aspirin (or its bioequivalents) included within the composition. |
| Carotenoid Complex | 1250 IU | 2500 IU | 1250 IU | | | | |
| Beta Carotene | 250 IU | 500 IU | 250 IU | | | | |
| Alpha Carotene | 100 mcg | 400 mcg | 100 mcg | | | | |
| Lutein | 400 mcg | 400 mcg | 50 mcg | | | | |
| Lycopene | 400 mcg | 400 mcg | 1000 mcg | | | | |
| Zeaxanthin | 20 mcg | 20 mcg | 50 mcg | | | | |
| Vitamin A | 3,000 IU | 2,000 IU | 1,500 IU | | | | |
| Vitamin B1 (Thiamine HCl) | 4 mg | 3 mg | 200 IU | | | | |
| Vitamin B2 (Riboflavin) | 5 mg | 2 mg | 1 mg | | | | |
| Niacinamide | 33 mg | 7 mg | 1 mg | | | | |
| Pantothenic Acid (d-Calcium Pantothenate) | 15 mg | 10 mg | | | | | |
| Vitamin B6 (Pyridoxine HCl) | 15 mg | 12.5 mg | | | | | |
| Biotin | 6 mg | 40 mg | 3 mg | | | | |
| Folic Acid | 150 mcg | 15 mg | 6 mg | | | | |
| Vitamin B12 (Cobalamin) | 300 mcg | 300 mcg | 200 mcg | | | | |
| Vitamin C* (Buffered Calcium Ascorbate, Ascorbic Acid and Ascorbyl Palmitate) | 6 mg | 6 mg | 3 mcg | | | | |
| Vitamin D3 (Cholecalciferol) | 150 mg | 600 mg | 100 mg | | | | |
| Vitamin E (d-alpha Tocopheryl Succinate) | 300 IU | 200 mg | 200 mg | | | | |
| Calcium (Carbonate, Ascorbate) | 70 IU | 30 IU | 100 IU | | | | |
| Chromium | 200 mg | 450 mg | 15 mcg | | | | |
| Copper (Gluconate) | 80 mcg | 70 mcg | | | | | |
| Iron (Ferrous Fumarate) | 0.5 mg | 0.5 mg | | | | | |
| Magnesium (Oxide) | 12 mg | 3 mg | 25 mg | | | | |
| Manganese (Gluconate) | 100 mg | 200 mg | | | | | |
| Selenium (L-Selenomethionine) | 4 mg | | 20 mcg | | | | |
| Zinc (Sulfate and Gluconate) | 25 mcg | 50 mcg | | | | | |
| Odorless Garlic | 5 mg | 7 mg | | | | | |
| Coenzyme Q-10 | 25 mg | — | 25 mg | | | | |
| L-Carnitine | | | 50 mg | | | | |
| Grape Seed Extract | | | 25 mg | | | | |
| Green Tea Extract | | | 25 mg | | | | |
| Quercetin | | | 50 mg | | | | |
| Hawthorne Berries* (Flavones) | | | 2 mg | | | | |
| Alpha Lipoic Acid | | | 30 mg | | | | |

The present invention may, of course, be carried out in other specific ways than those herein set forth without departing from the spirit and essential characteristics of the present invention. The present embodiments are, therefore, to be considered in all respects as illustrative and not restrictive and any changes coming within the meaning and equivalency range of the appended claims are to be embraced therein.

Having described my invention, we claim:

1. A method of providing micronutrient and acetylsalicylic acid supplementation needed for both the treatment of nutritional losses and deficiencies and the reduction of the risk of coronary heart disease said method comprising: administering concomitantly to a human on a daily basis an effective amount of multivitamins and minerals and an effective amount of acetylsalicylic acid, wherein the effective amount of multivitamins and minerals comprises:

| | |
|---|---|
| Vitamin B-1 | about 0.7 to about 15 mg |
| Vitamin B2 | about 0.7 to about 15 mg |
| Vitamin B6 | about 2.0 to about 100 mg |
| Niacin | about 6.0 to about 100 mg |
| Folate | about 50.0 to about 800 mcg |
| Pantothenic Acid | about 4.0 to about 50 mg |
| Vitamin B12 | about 0.5 to about 40 mcg |
| Biotin | about 5.0 to about 300 mcg |
| Calcium | about 100.0 to about 1,500 mg |
| Magnesium | about 25.0 to about 500 mg |
| Iron | about 1.0 to about 20 mg |
| Zinc | about 5.0 to about 30 mg |
| Manganese | about 1.0 to about 10 mg |
| Selenium | about 10.0 to about 200 mcg |
| Chromium | about 10.0 to about 300 mcg |
| Copper | about 0.0 to about 4 mg |
| Coenzyme Q-10 | about 5.0 to about 300 mg |
| Vitamin A | about 200.0 to about 15,000 IU |
| Beta Carotene | about 500.0 to about 15,000 IU |
| Alpha Carotene | about 50.0 to about 2,000 mcg |
| Lycopene | about 50.0 to about 10,000 mcg |
| Lutein | about 50.0 to about 5,000 mcg |
| Zeaxanthin | about 5.0 to about 500 mcg |
| Vitamin C | about 20.0 to about 1,000 mg |
| Vitamin D | about 0.0 to about 400 IU |
| Vitamin E | about 5.0 to about 2,000 mg |
| Grape Seed Extract | about 0.0 to about 300 mg |
| Green Tea Extract | about 0.0 to about 500 mg |
| Crataegus Oxyacantha Extract | about 0.0 to about 500 mg |
| L-carnitine | about 0.0 to about 700 mg |
| Alpha Lipoic Acid | about 0.0 to about 750 mg |
| Taurine | about 15.0 to about 1,000 mg |
| Quercitin | about 0.0 to about 500 mg, and |
| Garlic | about 0.0 to about 500 mg. |

* * * * *